United States Patent [19]

Sommadossi

[11] Patent Number: 5,464,748
[45] Date of Patent: Nov. 7, 1995

[54] METHOD OF DETECTING AND MONITORING LEVELS OF 3'-AMINO-3'-DEOXYTHYMIDINE IN BODY FLUIDS AND ANTIBODIES FOR SAME

[75] Inventor: Jean-Pierre Sommadossi, Birmingham, Ala.

[73] Assignee: The UAB Research Foundation, Birmingham, Ala.

[21] Appl. No.: 117,245

[22] Filed: Sep. 7, 1993

Related U.S. Application Data

[63] Continuation of Ser. No. 835,234, Feb. 13, 1992, abandoned.

[51] Int. Cl.$^6$ ................................................. G01N 33/531
[52] U.S. Cl. ................................. 435/7.7; 435/6; 435/7.1; 435/7.9; 435/7.92; 435/7.93; 435/974; 436/544; 436/815
[58] Field of Search .................. 435/6, 7.7, 974, 435/975, 7.1, 7.9, 7.92, 7.93; 436/543, 546, 547, 548, 545, 501, 544, 815; 530/388.21

[56] References Cited

U.S. PATENT DOCUMENTS

| | | | |
|---|---|---|---|
| 4,824,941 | 4/1989 | Gordon et al. | 530/403 |
| 5,051,361 | 9/1991 | Steinglein et al. | 435/79 |

OTHER PUBLICATIONS

Cretton "In Vitro and In Vivo Catabolism of the Anti-HIV 2',3'-di deoxynucleoside, 3'-Azido-3'-Deoxythymidiol (AZT) (Immune Deficiency)" Dissertation Abstract (1991).
Voller et al Alternative Immunoassays Ed W. P. Collings John Wiley & Sons (1985) pp. 77–86.
Tadepalli et al Clin Chem 36/6, 879–900 (1990).
"Pharmacokinetics of 3'-Azido-3'Deoxythymidine . . . in Rhesus Monkeys;" Antimicrob. Chemother.; Cretton et al.; v. 35, pp. 801–807. (1991).
"Catabolism of 3'-Azido-3'-deoxythymidine . . . for Human Bone Marrow Cells;" Mol. Phar.; Cretton et al.; v. 39, pp. 258–266. (1991).
"Determination of Zidovudine . . . Fluoroimmunoassay;" J. AIDS; Tadepalli et al.; v. 3, pp. 19–27. (1990).
"Tissue Distribution and Metabolic Disposition of Zidovudine in Rats;" Drug Metab. & Disp.; De Miranda et al.; v. 18, pp. 315–320. (1990).
"Fluorescence Polarization Immunoassay for Zidovudine;" Anti. Agents & Chem.; Granich et al.; v. 33, pp. 1275–1279. (1989).
"Radioimmunoassay for Retrovir . . . Virus Drug;" J. Immunoessays; Quinn et al.; v. 10, pp. 177–189. (1989).
"A Radioimmunoassay Procedure . . . in Plasma or Serum;" Pharm. Res.; Nerenberg et al.; v. 3; pp. 112–115. (1986).
"A Sensitive Radioimmuno-ssay . . . Guanine;" Anal. Biochem.; Quinn et al.; v. 98, pp. 319–328. (1979).
"Activities of 3'-Azido-3'Deoxythymidine . . . Human Immunodeficiency Virus Type I"; Antimicrob. Chemother.; Schinazi et al.; v. 34, pp. 1061–1967. (1990).
Product Brochure entitled ZDV-Trac 125/RIA Kit by incstar.
Product Brochure entitled AZT FPIA Reagent Set by Sigma Diagnostics.

*Primary Examiner*—Toni R. Scheiner
*Assistant Examiner*—Lora M. Green
*Attorney, Agent, or Firm*—Lahive & Cockfield; William C. Geary; Matthew P. Vincent

[57] ABSTRACT

Immunoassay techniques for quantitating the amount of 3'-amido-3'-deoxythymidine (AMT) in body fluid samples, and antibodies useful in performing such immunoassays, are provided. The immunoassays use antibodies which are specific to AMT and have no cross-reactivity with 3'-azido-3'-deoxythymidine (AZT). Moreover, there is provided an improved method of conducting AZT therapy wherein the concentration of both AZT and AMT is monitored and the AZT dosage is adjusted to maintain rather low concentrations of AMT.

13 Claims, No Drawings

METHOD OF DETECTING AND MONITORING LEVELS OF 3'-AMINO-3'-DEOXYTHYMIDINE IN BODY FLUIDS AND ANTIBODIES FOR SAME

BACKGROUND OF THE INVENTION

The U.S. Government has rights in this invention pursuant to NIH Grant No. HL 42125. This application is a continuation of application Ser. No. 835,234 filed on Feb. 13, 1992, abandoned.

The invention relates to immunoassays and detection kits used to monitor quantities of 3'-amino-3'-deoxythymidine (AMT) in body fluids. The invention also provides AMT specific antibodies useful with the immunoassays and detection kits, and to a method of improving AZT therapy by monitoring the concentration of AMT in body fluids of patients receiving AZT treatments.

Presently, 3'-azido-3'-deoxythymidine (AZT) is the only first line drug approved for the treatment of Acquired Immune Deficiency Syndrome (AIDS). AZT treatment of Human Immunodeficiency Virus (HIV) infected patients has yielded clinical benefits, including increased survival, decreased number of opportunistic infections, and partial improvement in neurologic manifestations. AZT has also been used, in combination with 5-fluorouracil, in treating colon carcinoma. Unfortunately, AZT treatment is limited by its toxicity to bone marrow cells, manifested by anemia and neutropenia.

Because of the importance of AZT therapy, a greater understanding of the pharmacodynamics and pharmacokinetics of AZT is essential. In particular, the mechanism responsible for the side effects associated with AZT therapy must be understood.

In humans, AZT is primarily eliminated as the 5'-O-glucuronide of AZT (GAZT), with 60–80% of an administered AZT dose being detected in urine as this catabolite. GAZT is not believed to possess any antiviral activity, nor is it believed to contribute to the adverse side effects associated with AZT therapy. However, it has recently been discovered that another hepatic catabolite of AZT is 3'-amino-3'-deoxythymidine (AMT). A greater understanding of this catabolite and its impact on AZT therapy may lead to improvements in AZT therapy. Cretton et al, *Molecular Pharmacology* 39:258–266 (February 1991); Cretton et al, *Antimicrobial Agents and Chemotherapy*, Vol. 35, No. 5, pp. 801–807 (May 1991). In the course of studying the pharmacokinetics and pharmacodynamics of AZT and AMT in humans receiving AZT, it will be necessary to quantitate the levels of both AZT and AMT in the body fluids of patients receiving this treatment. There is no suitable analytical methodology currently available to rapidly and effectively quantitate AMT levels in body fluids following the administration of AZT.

As with any drug, and especially one such as AZT which has serious side effects at high dosage levels, the formal establishment of a therapeutic range for a patient being treated with the drug is highly desirable. The recognized methods for measuring AZT plasma levels include the use of high performance liquid chromatography (HPLC) which is a reasonably sensitive and precise technique. However, although HPLC can be used for measuring AZT concentrations in noninfective samples and in HIV-positive samples, the HPLC method is not practical for the frequent monitoring of AZT in HIV-positive samples due to the exposure of reuseable parts, such as columns and pumps, to infectious material. Other disadvantages of HPLC for such applications include the relatively long analysis time required, elaborate sample preparation requirements, the need for relatively large sample size (500 µl), interference by body fluid components in the sample, and high cost.

Immunoassays are commonly used to quantitate the levels of therapeutic agents in body fluids. While many immunoassay techniques are known in the art, none is available for detecting and monitoring AMT levels. U.S. Pat. No. 5,051,361 discloses immunoassay methods, and antibodies useful in practicing such methods, for determining the levels of AZT in a sample of body fluid. While useful in assaying a sample for AZT, the methods and antibodies disclosed in the '361 patent cannot be used to measure AMT concentrations in a sample.

There is thus a need to provide rapid, sensitive and reliable methodologies for monitoring and quantitating AMT concentrations in relatively small samples of body fluids.

Accordingly, it is an object of the invention to provide a technique for detecting AMT concentrations in samples of body fluids. Another object of the invention is to provide such a technique which is cost effective and which is able to be performed frequently on a large number of samples while obtaining results relatively quickly. A further object is to provide antibodies useful in such an immunoassay for AMT which are highly specific to AMT and have no cross-reactivity to AZT and similar compounds. Yet another object is to provide a detection kit which enables AMT and GAMT concentrations to be monitored in samples of body fluids. It is also an object to provide an improved dosage regimen for efficiently treating patients with AZT so as to minimize the adverse side effects associated with AZT therapy. Other objects will be apparent upon reading the description which follows.

SUMMARY OF THE INVENTION

The present invention relates to improved methods of AZT therapies, as well as to diagnostic methods and antibodies for use in such methods for detecting AMT concentrations in body fluids. In one aspect, the invention relates to a method of defining an efficient treatment regimen for administering AZT. It has been discovered that 3'-amino-3'-deoxythymidine (AMT) and its 5'-O-glucuronide (GAMT) are significant catabolites of AZT. Further, AMT has been found to be an agent many more times toxic to granulocyte macrophage colony-forming units (CFU-GM) and erythroid burst-forming units (BFU-E) than is AZT. In fact, AMT is believed to be the agent mainly responsible for the toxic effects associated with AZT treatment. AMT is also believed to interfere with the antiviral activity of AZT. According to the method of the invention, AZT therapy is enhanced, and its side effects minimized, by monitoring both AMT and AZT levels within a body fluid of a subject, and adjusting the AZT dosage in response to the concentration of AMT.

In another embodiment the invention relates to a method of analyzing a sample of a body fluid to detect and measure the concentration of AMT. For instance, a sample of a body fluid is mixed with a tracer compound comprising an AMT analog having attached thereto a label group able to be detected, and an antibody having a high degree of specificity to AMT and no cross-reactivity to AZT. Following a suitable incubation period, an immunoassay technique is utilized to detect the amount of tracer compound bound to the antibody. The amount of AMT present in the sample can then be calculated based on the amount of tracer bound to the antibody. This technique has sensitivity limits as low as about 0.1 to 1.0 ng/ml.

Further, the invention provides an antibody, either monoclonal or polyclonal, which has a high degree of specificity to AMT and no cross-reactivity to AZT, GAZT, naturally occurring purines and pyrimidines, or other purine and pyrimidine analogs, including therapeutic agents. The antibody is prepared in response to an immunogen which comprises an analog of AMT linked to a carrier. The AMT analog used to form the immunogen preferably has a general formula as follows:

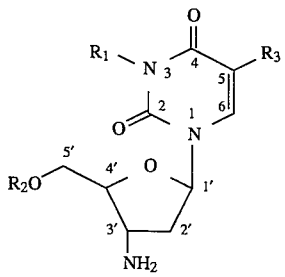

where $R_3$ is $CH_3$ or H and one of $R_1$ and $R_2$ is hydrogen and the other is R-Y, where R is a linking group and Y is a carrier. Alternatively, $R_1$ and $R_2$ are hydrogens and $R_3$ is R-Y, where R is a linking group and Y is a carrier. The linking group can be selected from among many functional groups, including succinyl, aminoalkyl, alkyl, carboxyl, and hydroxy. The carrier can be selected from albumins, serum proteins, and polyamino acids. Particularly useful carriers include bovine serum albumin (BSA), rabbit serum albumin (RSA) and thyroglobulin (TG). Exemplary immunogens include AMT-3-valeryl:BSA, AMT-3-valeryl:RSA, AMT-5'-succinyl:BSA, AMT-5'-succinyl:RSA, AMT-5-carboxyethyl:TG, and AMT-5-methylamido:BSA.

While the method of the invention detects and quantitates AMT, it may also be used to detect for analogs of AMT.

DETAILED DESCRIPTION OF THE INVENTION

3'-azido-3'-deoxythymidine (AZT) is now an important therapeutic agent primarily useful in AIDS treatments, but also useful in treating various carcinomas, including colon carcinoma. Through studies of the pharmacokinetics and metabolism of AZT, it has been discovered that, in addition to GAZT, two previously unidentified hepatic catabolites of AZT exist. These are 3'-amino-3'-deoxythymidine (AMT) and its 5'-O-glucuronide (GAMT). Further studies have determined that AMT is highly toxic to human bone marrow cells. Indeed, AMT is five to seven more times toxic to human bone marrow cells than is AZT, and it is believed to be the agent mainly responsible for the toxic effects associated with AZT therapy. In addition, at concentrations as low as a 1:1 molar ratio with AZT, AMT has an adverse effect on the antiviral activity of AZT.

As noted, AMT is a human hepatic catabolite of AZT. However, AMT analogs may also result from the catabolism of other compounds including AZT analogs having an azido functional group at the 3' position of the sugar moiety which is reduced to an amino functional group. Generally, all 3'-azido-2',3'-dideoxynucleosides will be catabolized at the hepatic site to yield the 3'-amino analog. Examples of such 3'-azido-2',3'-dideoxynucleosides include 3'-azido-2',3'-dideoxyuridine (AZdU); 3'-azido-2',3'-dideoxycytidine (AZdC); 3'-azido-2',3'-dideoxy-5-methylcytidine (AZd5-MC); and 3'-azido-2',3'-dideoxyguanosine (AZdG). Also, AMT and AMT analogs can be produced through the catabolism of other therapeutic agents, such as homodimers and heterodimers of AZT and AZT analogs, other deoxythymidines and nucleoside analogs. The heterodimers include AZT and AZT analogs as one molecule of the dimer. Examples of such dimers include 3'-azido-3'-deoxythymidilyl-(5',5')- 2,3'-dideoxy-5'-adenylic acid (AZT-P-dda); 3'-azido-3'-deoxythymidilyl-(5',5')-2',3'-dideoxy-5'-i nosinic acid (AZT-P-ddI), the corresponding 2-cyanoethyl cogenes, AZT-P(CyE)-ddA; AZT-P(CyE)-ddI; and 3'-azido-3'-deoxythymidilyl-(5',5')-3'-azido- 3'-deoxythymidilic acid (AZT-P-AZT).

In view of these findings, there is a need to develop reliable and efficient methodologies for monitoring the concentration of AMT and AMT analogs in body fluids such as a blood plasma, plasma, urine, bile and semen.

In one embodiment of this invention a sample of a body fluid containing or suspected of containing AMT or an AMT analog is mixed with (i) a tracer compound comprising an analog of AMT having attached thereto a label group able to be detected, and (ii) an antibody (or a binding fragment thereof) having a high degree of specificity to AMT (or the AMT analog) and to the tracer compound and no cross-reactivity to AZT. The term antibody is herein defined to mean an intact antibody or a suitable binding fragment thereof, including F(ab) and F(ab)$_2$ fragments, as well as single chain antibodies. The AMT present in the sample and the tracer compound compete for a limited number of antibody binding sites, resulting in the formation of AMT-antibody and tracer-antibody complexes. By maintaining the concentration of tracer compound and antibody constant, the amount of tracer-antibody complex formed is inversely proportional to the amount of AMT present in the sample. A quantitative determination of the level of AMT present in the sample is then made, based on the amount of tracer-antibody complex in the reaction mixture.

In another embodiment of this invention, an antibody, or binding fragment thereof, having a high degree of specificity to AMT and no cross-reactivity to AZT, is attached to the surface of an insoluble material. The fixed antibody is then incubated with a sample of a body fluid suspected of containing AMT for a period of time sufficient for the association of antibody:AMT conjugates to reach equilibrium. The fixed antibody is then washed such that free AMT is removed, while antibody-bound AMT is retained. The antibody:AMT conjugate is then incubated with a labeled secondary antibody specific for an epitope of AMT, spatially located such that binding of both the first and second antibody can occur simultaneously. A preferred secondary antibody recognizes an epitope on the pyrimidine ring. Unbound labeled secondary antibody is washed away and the bound labeled secondary antibody remaining is measured. The amount of bound labeled secondary antibody is proportional to the amount of AMT present in the body fluid. This type of immunoassay, unlike competitive immunoassays, does not require the tracer molecule to be an analog of AMT, rather detection is carried out by a labeled secondary antibody.

The concentration of AMT in the sample assayed will vary from about 10 to 500 ng/ml depending on the therapeutic dosage of AZT administered. The concentration of AMT in a given sample will vary depending upon factors such as the body fluid sample evaluated, the dosage of AZT administered, the elapsed time since the AZT administration, and factors which may influence AZT metabolism in an individual. The sensitivity of the assay may thus be adjusted to account for such variations, but generally the assay should be of sufficient sensitivity to detect and quantitate AMT at concentrations as low as 0.1 to 1.0 ng/ml.

It is also possible to determine the level of 3'-amino-3'-deoxythymidine glucuronide (GAMT) in a sample of body fluid by first converting GAMT to AMT. To accomplish this, the enzyme β-glucuronidase is useful in that it acts to catalytically remove the 5'-O-glucuronide from GAMT. The level of GAMT is represented by the difference of the concentration of AMT before and after treatment with β-glucuronidase.

The invention is not limited to a particular assay procedure, and therefore is intended to include both homogeneous and heterogeneous procedures. Exemplary immunoassays which can be conducted according to the invention include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). The indicator moiety, or label group, is selected so as to meet the needs of various users of the method which are often dictated by the availability of assay equipment and compatible immunoassay procedures. Among the most preferred immunoassays are the FPIA and RIA methodologies.

General techniques to be used in performing the various immunoassays noted above are known to those of ordinary skill in the art. Moreover, a general description of these procedures is provided in U.S. Pat. No. 5,051,361 which is incorporated herein by reference. Nevertheless, a brief review of immunoassay techniques is provided below.

Homogeneous immunoassays are assays which do not require the separation of antibody bound tracer from free tracer. The antigen-antibody interaction causes, directly or indirectly, a measurable change in the signal obtained from the label group of the tracer.

The preferred homogeneous assays are those utilizing an enzyme or a fluorescent reagent as a label group. Enzyme immunoassays are also preferred because they are quite sensitive and are therefore capable of measuring a lower AMT concentration. Both of these types of assays are also precise and easily automated. Further advantages of these assays include the relatively small sample size per assay, and assay results compare well with results obtained from an HPLC assay.

One Example of a homogeneous immunoassay useful in practicing the method of the invention includes fluorescence polarization immunoassays (FPIA) in which the degree of polarization of fluorescent light emitted from the sample increases in proportion to the bound, fluorescently labeled AMT analog. Others include substrate-labeled fluorescent immunoassays in which binding of the labeled AMT analog affects the release of a fluorescent group from the labeled AMT analog; fluorescence quenching and fluorescence enhancing immunoassays in which the level of fluorescence of the labeled AMT analog is affected by its binding to the antibody; and enzyme-linked immunoassays in which the activity of the enzyme is modulated by antibody binding.

Heterogeneous immunoassays are assays that require the separation of bound tracer from free tracer prior to determining the amount of ligand in the sample. Among the preferred heterogeneous immunoassays are those with a radioactive or enzyme group as the label group. These are preferred as they are precise, easily automated, require only a small sample size and are generally among the most sensitive.

Radioimmunoassays (RIA) are heterogeneous immunoassays utilizing radioactively labeled ligands. For example, AMT can be directly labeled with $^3$H, or $^{14}$C, or an AMT analog can be labeled with $^{125}$I. Labeled AMT competes with unlabeled AMT from the sample for a limited number of antibody binding sites. After the bound complex of labeled AMT-antibody and AMT is separated from the unbound (free) labeled AMT, the radioactivity in the bound fraction, or free fraction or both is determined in an appropriate radiation counter. The concentration of bound labeled AMT is inversely proportional to the concentration of unlabeled AMT present in the sample. The antibody to AMT can be in solution, and separation of free and bound AMT can be accomplished using agents such as charcoal, or a second antibody specific for the animal species whose immunoglobulin contains the antibody to AMT. Alternatively, antibody to AMT can be attached to the surface of an insoluble material. In this case, separation of bound and free AMT is performed by appropriate washing.

Immunoradiometric assays (IRMA) generally refer to heterogeneous immunoassays in which the antibody reagent is radioactively labeled. An IRMA requires the production of a multivalent AMT conjugate, by techniques such as conjugation to a protein e.g., rabbit serum albumin (RSA). The multivalent AMT conjugate must have at least 2 AMT residues per molecule and the AMT residues must be of sufficient distance apart to allow binding by at least two antibodies to the AMT. For example, in an IRMA the multivalent AMT conjugate can be attached to a solid surface such as a plastic sphere. Unlabeled AMT and antibody to AMT which is radioactively labeled are added to a test tube containing the multivalent AMT conjugate coated sphere. The AMT competes with the multivalent AMT conjugate for AMT antibody binding sites. After an appropriate incubation period, the unbound reactants are removed by washing and the amount of radioactivity on the solid phase is determined. The amount of bound radioactive antibody is inversely proportional to the concentration of AMT in the sample.

Another preferred heterogeneous immunoassay involves the use of enzyme labels such as horseradish peroxidase, alkaline phosphatase, luciferase, urease, and β-galactosidase. The heterogeneous EIA differs from the homogeneous EIA in that determination of the amount of ligand in the sample requires the separation of bound and free tracer. For example, AMT analogs conjugated to horseradish peroxidase compete with unlabeled AMT for a limited number of antibody combining sites present on antibodies to AMT attached to a solid surface such as a microtiter plate. The AMT antibodies may be attached to the microtiter plate directly after fractionating antiserum containing AMT antibodies with ammonium sulfate or indirectly by first coating the microtiter plate with multivalent AMT conjugates (coating antigens) prepared for example by conjugating AMT with serum proteins such as rabbit serum albumin (RSA). After separation of the bound labeled AMT from the unbound labeled AMT, the enzyme activity in the bound fraction is determined spectrophotometrically at a fixed period of time after the addition of substrate.

Alternatively, the antibody, attached to a surface such as a microtiter plate or polystyrene bead, is uncubated with appropriately prepared serum or another bodily fluid. AMT present in the fluid will be bound by the antibody in a manner dependent upon the concentration of AMT and the association constant between the two. After washing, the antibody/AMT complex is incubated with a second antibody specific for a different epitope on AMT distal enough from the AMT-specific antibody binding site such that steric hinderence in binding of two antibodies simultaneously to AMT may be accomplished. For example, the second antibody may be specific for a portion of the pyrimidine ring of the AMT molecule. The second antibody can be labeled in a manner suitable for detection, such as by radioisotope, a fluorescent compound or a covalently linked enzyme. The amount of labeled secondary antibody bound after washing away unbound secondary antibody is proportional to the amount of AMT present in the serum or other bodily fluid.

The above examples of preferred heterogeneous immunoassays describe the use of radioactively and enzymatically labeled tracers. Assays other than EIA which exploit nonisotopic detection systems are also known. The labels used with such assays include fluorescent materials such as fluorescein and analogs thereof, 5-dimethylaminonaphthalene-1-sulfonyl derivatives, rhodamine and analogs thereof, coumarin analogs, and phycobiliproteins such as allophycoryanin and R-phycoerythrin; phosphorescent materials such as erythrosin and europium; luminescent materials such as luminol and luciferin; and sols such as gold and organic dyes.

Variations to the above described assay designs will be obvious to those skilled in the art.

As noted above, tracer compounds useful in practicing the immunoassay methods of the invention may be prepared from AMT analogs having attached thereto a suitable label group which emits a detectable signal. Various label groups can be used, depending on the type of immunoassay conducted. Useful labels include those which are fluorescent, radioactive, phosphorescent, chemiluminescent, bioluminescent, and free radical. Also, the label groups may include polypeptides (e.g., enzymes or proteins), polymers, polysaccharides, receptors, cofactors, and enzyme inhibitors.

AMT analogs preferably are prepared such that the analog has one or more antigenic determinant sites capable of binding to a receptor (AMT antibody) during the course of the immunoassay. The AMT analog must, of course, possess sufficient structural similarity to AMT so as to be recognized by and be bound to the AMT antibody. The AMT analog may then be coupled with label groups.

The tracer compound of the invention comprises an AMT analog of the structure

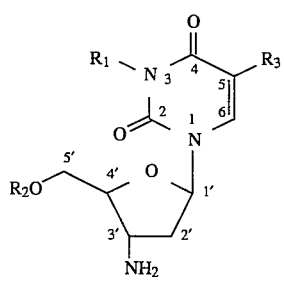

where $R_3$ is $CH_3$ or H, and one of $R_1$ and $R_2$ may be H and the other may be R-X, where R is a linking group and X is the label group which emits a signal able to be detected. Alternatively, $R_1$ and $R_2$ are hydrogens and $R_3$ is R-X. In a radioimmunoassay using $^3H$ or $^{14}C$ as the label group, a linking group is not necessary as the tritium or $^{14}C$ may be incorporated directly into the AMT molecule. Tritium may be incorporated at virtually any location on the AMT molecule, however it is preferably incorporated at the methyl group attached at the 5 position or at the methylene protons at the 5' position of the ribose moiety. Similarly, $^{14}C$ may be incorporated at virtually any location on the AMT molecule. Preferred incorporation sites include positions 2 or 4, or at the methyl group at the 5 position.

The tracer compound useful with this invention may be prepared by coupling the AMT analogs described above with a suitable label group. Coupling can be accomplished by means known in the art. Furthermore, the identity of the label group is not critical to the invention and can be selected by those skilled in the art to fulfill the needs of a particular application.

AMT analogs preferably can be prepared by joining a linking group (R) to the AMT molecule at the 3, 5 or the 5' positions. The atoms comprising R can include 0–50 atoms. More preferably R comprises from 0–30 carbon atoms and from 0–25 heteroatoms selected from oxygen, nitrogen, sulfur and halogens. Exemplary functional groups which can form label group (R) include alkyl, carboxyl, carbonyl, nonoxocarbonyl, hydroxy, alkoxy, amido, halo, thiocarbonyl, cyano, nitrilo, thio, imino, amino, carbalkoxy, mecuri, phthalimido, formyl, keto, succinimidoxy, thiocarbamyl, azo, hydroxyphenyl, succinyl, and imidazolyl, as well as other saturated or unsaturated carboxylic or heterocyclic rings.

Other linking groups will be apparent to those skilled in the art. The importance of the linking lies in its ability to conjugate the AMT analog with a suitable carrier for use as an immunogen or as a tracer molecule. To this end, the reaction conditions under which derivatization of the AMT analogs takes place must account for the presence of the free amino group at the 3' position of the ribose moiety. Where derivation is to occur at the 5' position, the synthesis reactions can be conducted under acidic conditions (e.g., pH 4 to 5) and/or under protecting conditions of the amino group at the 3' position. These procedures are sufficient to prevent reaction with this amino group.

In addition, other reactive linking groups are known in the art. For instance, sulfhydryl and aldehyde/ketone reactive linkers can be utilized with the appropriate AMT analogs.

There are numerous isotopes known in the art which are suitable for use in those assays which require detection of radioactivity, such as Radioimmunoassays. These isotopes include $^3H$, $^{14}C$, $^{35}S$, $^{32}P$, $^{125}I$ and $^{131}I$, which are convenient for routine lab use.

A preferred radioimmunoassay technique, as noted above, uses tritiated AMT, with the $^3H$ label group attached at the 5' position of the sugar, or at the 3 or 5 position of the pyrimidine ring of AMT. The $^3H$ label preferably is attached at the methyl group of the 5 position. Incorporation of $^3H$, as well as $^{14}C$, into the structure of AMT can be carried out by routine synthesis. See for example Hill et al. (1988) J. Labelled Compounds and Radiopharmaceuticals 25:277; and Krenitsky et al. (1983) J. Med. Chem. 26:891, incorporated by reference herein. For $^{14}C$ incorporation, the preferred positions are the 2 and 4 positions of the pyrimidine ring and the 5-methyl group.

Another RIA technique can utilize $^{125}I$ as the label group. Preferably, the $^{125}I$ label is attached, by way of a linking group, at the 5-methyl position of the pyrimidine ring. Preferred linking groups are 5-Iodo-4-imidazolethylamine ($^{125}I$-Histamine), or radioiodinated tyrosine methyl esters. Synthesis of tritiated AMT and $^{125}I$ labeled AMT can be accomplished through known techniques. Another preferred position for this label is the 3 position.

For FPIA techniques preferred fluorescent labels include FAM, FITC, FTED, and EITC. These preferably are attached at 3, 5 or 5' positions, through the various linking groups noted herein. Exemplary linking groups include valeryl, acetyl, propyl, butyryl, alkyl, aminoalkyl, propionyl, methylamido, acetylamido, carboxyethyl.

A preferred AMT tracer for an ELISA assay is AMT-5'-succinyl apoferitin. The sucinyl apoferitin group may be attached a the 3 and 5 positions as well.

Of particular significance to this invention is the ability to raise antibodies which specifically bind AMT, while not cross reacting with AZT, GAZT, naturally occurring purines and pyrimidines, or other purine or pyrimidine analogs, including therapeutic agents. The specificity of the antibody with regard to differentiating between these similar compounds rests entirely on the effect on binding of the amino substituent at the 3' position of the deoxyribose ring.

All immunoassay methods require an antibody raised to the ligand or a closely related ligand analog. AMT is a ligand which, due to its low molecular weight (less than 250 daltons), is unlikely to provoke an immune response by itself. Thus, it is preferably converted to an analog by attaching a linking group (R) to the AMT molecule, at either the 3, 5 or 5' position, as described above. Subsequently, the AMT analog is conjugated to a carrier which is immunogenic in animals. Preferred carriers include proteins such as albumins, serum proteins (e.g., globulins and lipoproteins), and polyamino acids. Examples of useful proteins include bovine serum albumin, rabbit serum albumin, thyroglobulin, keyhole limpet hemocyanin, egg ovalbumin and bovine gamma-globulins. Synthetic polyamino acids such as polylysine or polyarginime are also useful carriers. Carbodiimide-mediated dehydrations form one technique useful for the preparation of these conjugates. Another preferred conjugate preparation technique is by acylation of amines with active esters. The later conjugation technique may result in a better immunological response to the immunogen due to a higher incorporation rate of AMT analog to carrier.

The preparation of the immunogens or conjugates of AMT analogs can be accomplished by means known in the art. See for example, *Principles of Competitive Protein Binding Assays*, 2nd Ed, Odell et al. editors, John Wiley and Sons, N.Y. 1983, Chapter 4, "Conjugation Techniques/Chemistry" and the references discussed therein. Acceptable procedures for the preparation of nucleoside analog immunogens are also disclosed in the U.S. Pat. No. 5,051,361; Nerenberg et al. 1986 Pharmaceutical Research 3:112; Quinn et al. 1979 Analytical Biochemistry 98:319 and references cited therein.

The immunogens may be prepared by first forming an AMT analog using the various linking groups described above with respect to the tracer compound. Thereafter the AMT analog is conjugated to a carrier. Exemplary immonogens include AMT-3-carboxyethyl:Y; AMT-3-valeryl:Y; AMT-3-succinyl:Y; AMT-3-propionyl:Y; AMT-3-butyryl:Y; AMT-5-methylamido:Y, AMT-5-carboxyethyl:Y; AMT -5'-valeryl:Y; AMT-5'-butyryl:Y; AMT-3-acetyl; AMT-3-propyl; AMT-5'-propionyl:Y; and AMT-5'-succinyl:Y, where Y represents a carrier selected from the group consisting of BSA, RSA, TG, PL, and PA. In the above examples Y designates a carrier and may include all of the potential carrier previously mentioned. The preferred carriers include BSA, RSA and thyroglobulin. It is noted that the above immunogens are merely exemplary and should not be read to limit the immunogens which may be used with the invention.

The preparation of specific antibodies using immunogens of the type described above may be accomplished by techniques known to those skilled in the art. In the usual case, a host animal such as a rabbit, goat or mouse is injected at one or more sites with the immunogen, normally emulsified with an adjuvant. Further injections are made at the same or different site or sites at regular or irregular intervals. The animal's immune system will respond to the immunization by producing antibodies that will react with one or more epitopes of the conjugate.

Each plasma cell clone secretes a unique antibody (idiotype). Monoclonal antibodies are produced in vitro by physically separating the individual plasma cell clones which have been hybridized with a tumor cell line, thus enabling one to produce antibodies of a selected idiotype over an extended period of time.

In the animal, generally multiple plasma cell clones are produced, resulting in a heterogeneous mixture of antibodies (i.e., polyclonal antibodies) in the blood. After the blood has been collected, it will clot and the clot may be removed. The remaining liquid or serum, which contains the polyclonal antibodies is referred to as antiserum.

Although generally not required, purification of the antiserum may be instituted where it is useful to remove undesired material, such as non-specific antibodies, before the antiserum used in performing assays.

It is to be noted that while monoclonal antibodies from a particular monoclonal line developed are identical and the polyclonal antibodies obtained from a particular animal injected are similar, some variance in antibody binding properties does exist between antibodies from different monoclonal lines and/or different animals injected. Identical construction of the AMT analog portion of the tracer and of the immunogen can result in antibody binding to the tracer so great that AMT cannot effectively compete with the tracer for binding to the antibody. Accordingly, when an antibody population is evaluated, a number of tracers are made in which the length and/or composition of the group attaching the indicator moiety to AMT is varied in order to optimize the binding properties of the antibodies versus the tracer compound and AMT.

There are a number of immunoassays useful for the detection and quantitation of the level of AMT in a body fluid. As set forth above, the principal goal in the immunoassays is to differentiate between AMT and other thymidine analogs such as AZT which may be present in the body fluid. These immunoassays can include the competitive binding assays, such as those taught herein, where a labeled AMT analog is used as a tracer molecule. Alternatively, assays wherein a labeled secondary antibody is used are also useful in determining the level of AMT. The preferred immunoassays are radioimmunoassays (RIA) in which the AMT analog tracer is labeled with either $^3$H, $^{14}$C or $^{125}$I for detection, as well as fluoresense polarization immunoassays (FPIA), where the tracer molecule comprises a fluorescent compound conjugated to AMT or an AMT analog such that binding of the AMT moiety of the tracer molecule effects the fluoresense polarization of the tracer.

Generally, the immunoassays conducted according to the present invention utilize sample sizes ranging from about 50 to 200 μl. The sensitivity range of the immunoassay, as noted above, is as low as about 0.1 to 1.0 ng/ml. The incubation period should be suitable to enable antibody/ligand complexes to form and reach equilibrium.

Diagnostic test kits can be developed which are useful for conducting the immunoassay techniques of this invention. Such kits enable immunoassays to be quickly conducted with minimal user preparation. The diagnostic kits can be used for the determination of the presence or absence of AMT in a sample of biological fluid as well as determining the level of AMT in a sample containing AMT. These kits will generally include a set of optimized reagents comprising the combination of antibodies specific to AMT (and not cross reactive with AZT and related compounds) and tracer compound capable of reacting with the antibodies to produce a detectable antibody-tracer complex. The antibodies preferably are intermixed with the tracer and a sample of biological fluid to be tested, and then subjected to the appropriate technique for indicating the presence of AMT in the sample.

In addition, the diagnostic test kits of this invention may optionally contain a precipitating agent, as described herein, suitable for reducing nonspecific background interference, for example fluorescence, due to the presence of various materials in the sample to be analyzed. The test kit may also be supplied with a buffer, as appropriate for the particular assay to which the kit is directed. The test kit may further be supplied with means for separating the antibody-tracer complex from unbound or free tracer in the case where a heterogeneous assay method is used.

The relation between dose of AZT and the clinically observed response is often quite complex. Typically, the primary concern in an AZT treatment regimen is the effect of the treatment on the patient's disease. However, manifestations of any therapeutic effect are not immediately detectable. Various pharmacokinetic processes determine the amount of time required before the drug appears at the target site, as well as the concentration at which the drug appears, and for how long the drug will remain at the target sites. Input, distribution, metabolism and loss are the major pharmacokinetic variables. Moreover, several pathologic and physiologic processes dictate dosage adjustment in individual patients.

Pharmacokinetics plays a role in the dose efficacy scheme by providing the quantitative relationship between drug efficacy and drug dose, with the aid of measurement of drug concentrations in various bodily fluids. The importance of pharmacokinetics in patient care rests upon the improvement in drug efficacy and reduction in toxicity that can be attained when the measurement of drug and drug metabolite levels in the general circulation is added to traditional methods of predicting the dose of the drug.

The "dosage" of AZT has typically been represented by a decision involving four variables:

(i) the amount of AZT to be administered at one time;

(ii) the route of administration;

(iii) the interval between doses;

(iv) the period of time over which AZT administration is to be continued.

With the present discovery of the significance of AMT as a human hepatic metabolite of AZT, the dosage of AZT must also take into account the concentration of AMT in body fluids during AZT therapy.

Calculation of the appropriate maintenance dose of AZT is a primary goal. Attainment of an appropriate maintenance dosage regimen often requires adjustment for that patient. For instance, the dose and frequency of administration required to achieve effective therapeutic blood and tissue levels vary in different patients because of individual differences in drug metabolism and elimination.

The present invention provides a method whereby one can monitor both the AZT and AMT levels in a given individual, and can adjust the dosage of AZT based upon the level of AMT in the body fluids. For instance, a clinician can prescribe a dosage regimen of AZT, wherein the dosage amounts and dose frequency are established such that the concentration of AMT in blood serum is minimized and does not exceed the level at which AMT toxicity becomes unacceptable. Typically, it is desirable to maintain the concentration of AMT below about 5 to 10 ng/ml, as opposed to the usual levels of about 50 to 200 ng/ml. Those skilled in the art will be able to ascertain from the clinical manifestations of toxicity, what the maximum tolerable AMT concentration for a given individual should be. In addition, those skilled in the art will recognize that the method of accounting for AMT levels in administering AZT is also applicable wherein a 3'-azido-2',3'-dideoxy nucleoside analog is used which results in a 3'-amino metabolite.

The follow examples serve to further illustrate the invention.

Example 1

The synthesis of 3'-amino-3'-deoxythymidyl- 5'-hemisuccinate (AMT-5'-HS) can be carried out as follows: a mixture of 267 mg AZT, 200 mg succinic anhydride, 200 μl pyridine and 25 mg 4-dimethylaminopyridine (DMAP) in 2 ml Tetrahydrofuran (THF) are stirred for 2 hours at room temperature. The bulk of the pyridine is then removed by coevaporation with $CHCl_3$. The residue is then taken up in 2 ml of MeOH, acidified with 200 μl HOAc and chromatographed by preparative TLC using the solvent system $CHCl_3$/MeOH/HOAc (90+10+0.1). The band containing the product is eluted with MeOH. The solvent is then evaporated and a UV spectra obtained of the AZT analog. Homogeneity of the product can be assessed by TLC. AZT-5'-HS and Triphenylphosphine (TPP) are dissolved in pyridine and the reaction solution is stirred at room temperature for 3 hrs. Concentrated ammonium hydroxide is then added and the solution is stirred for an additional 2 hrs. Pyridine is removed under reduced pressure, water is added and TPP and TPP oxide are removed by filtration. Evaporation of the filtrate leads to a solid residue, AMT-5'-H5. For instance, TLC will demonstrate whether the reaction product is AMT or a derivative. Characteristic absorption bands in its IR spectrum are useful in analyzing the reaction product, for instance an absorption peak at 3000 $cm^{-1}$ indicates the 3'-amino group is intact and the 3465 $cm^{-1}$ band present in the starting material (5'-OH) should be missing in the product. In addition, in detecting free amino groups can be used to verify the presence of the 3'-amino group. One such reagent useful to this end is Ninhydrin.

Example 2

The synthesis of N-[(3'-amino-3'-deoxythymid- 5'-yl)-succinyloxy]-succinimide (AMT-5'-S:NOS) can be accomplished as follows: the active ester is prepared by stirring a mixture of 87.1 mg of AMT-5'-HS(Example 1), 28.2 mg of N-hydroxysuccinimide (NOS) and 100 mg of 1,3-dicyclohexylcarbodiimide (DCC) in 3 ml of THF for 2 hours at room temperature. The percent conversion can be estimated by TLC and the mixture is used immediately without isolation of the ester.

Example 3

To prepare AMT-5'-succinyl:BSA (AMT-5'-S:BSA), a solution of 30 mg AMT-5'-HS (Example 1) in 2 ml N,N-dimethylacetamide (DMA) is diluted with 17 ml of 0.15M NaCl and added to 68 mg bovine serum albumin (BSA) dissolved in 25 ml deionized water. 36 mg of dry 1-ethyl-3-(3-dimethylaminopropyl)- carbodiimide hydrochloride (ECDI) is added with rapid stirring overnight at room temperature at pH 5.5. The reaction mixture is chromatographed over a column of Sephadex G-25 and eluted with PBS (0.01M $NaPO_4$/0.15M NaCl/pH 7.4). Sephadex is a registered trademark of Pharmacia Fine Chemicals, Inc.

Example 4

The synthesis of 5-[(3'-amino-3'-deoxythymid- 5'-yl)-succinamido]-fluorescein (AMT-5'-S:FAM) can be carried out as follows: a solution of 10 mg of AMT-5'-HS (Example 1), 10 mg fluoresceinamine (FAM), 1.5 μl concentrated HCl and 10 mg DCC in 2 ml of t-butanol is stirred for 30 minutes at room temperature. An aliquot of the reaction mixture can characterized by chromatography using TLC and the solvent system $CHCl_3$/MeOH/HOAc (90+10+1). The product band is scraped, eluted with MeOH and rechromatographed on RPF 250 um using the solvent system MeOH/$H_2O$/HOAc (40+60+3). The active product is then scraped and eluted with MeOH.

Example 5

To synthesize of 2-[(3'-amino-3'-deoxythymid- 5'-yl)-succinamido]-3-(4-hydroxyphenyl)-propionic acid methyl ester (AMT-5'-S:TME), a mixture of 22.5 mg AMT-5'-HS (Example 1), 15 mg NOS and 10 mg DCC in 550 μl THF are stirred for 2 hours at room temperature. A solution of 25 mg tyrosine methyl ester (TME) in 500 μl of THF/MeOH (9+1) is added to the reaction mixture and the resulting mixture stirred at room temperature for 4 hours. The solution is clarified by centrifugation, the supernatant evaporated and the residue taken up in $CHCl_3$, which is washed with 0.5% $NaHCO_3$, then 0.1M HCl. The organic layer is concentrated to a small volume, clarified by adding a small amount of MeOH and chromatographed by TLC using the solvent system MeOH/$H_2O$/HOAc (33+66+3). The product is scraped and eluted with MeOH/THF (1+1). A 25 μl aliquot of this eluate is diluted with 5 ml deionized water and filtered through a 0.45 um PTFE membrane. Analytical TLC using a solvent system of MeOH/$H_2O$/HOAc(33+66+2) allows verification of a homogeneous product.

Example 6

The synthesis of AMT-5'-succinyl:apoferritin (AMT-5'-S:APO) can be accomplished as follows: a solution of 23 mg horse spleen apoferritin in 5 ml borax-HCl buffer (0.075M, pH 8.5) is chilled on an ice bath and treated with a reaction mixture containing 50 μmoles of the freshly prepared AMT-5'-S:NOS (Example 2). The mixture is stirred at 0° to 15° C. for 1 hour, then at room temperature for 1 hour and chromatographed over Sephadex G-25.

Example 7

One method of preparing 5-(3'-amino-3'-deoxythymid-3-yl)-valeric acid methyl ester (AMT 3-MV) involves adding to a solution of 487 mg AMT, 500 μl sodium methoxide solution (4.4M NaOMe in MeOH) and 500 μl of methyl-5-bromovalerate (MBV) in 1 ml DMPU and stirring for 1 hour at 70° C. Another 200 μl each of NaOMe solution and MBV are added and the mixture stirred for another hour at 70° C. Then, a further 200 μl each of NaOMe solution (a total of 900 μl NaOMe solution) and 200 μl of MBV (a total of 900 μl MBV) are added and heated at 70° C. for another hour (total heating time of three hours). Analytical thin layer chromatography (TLC) on silica gel using the solvent system 2-propanol/HOAc/$H_2O$ (90+2+8) can be used to verify that no AMT remains in the reaction mixture. The mixture is diluted with 20 ml cold water, acidified with HOAc, extracted into EtOAc, concentrated to a small volume under reduced pressure at 45° C. and chromatographed by preparative TLC using the solvent system 2-propanol/HOAc/$H_2O$ (90+2+8). The band containing the product is eluted with MeOH and concentrated to an oil at 45° C. under reduced pressure. The product is analyzed for homogeneity by analytical TLC.

Example 8

The synthesis of 5-(3'-amino-3'-deoxythymid- 3-yl)-valeric acid (AMT-3-VA) can be carried out as follows: about 600 mg of the ester AMT-3-MV (Example 7) is dissolved in 5 ml MeOH and then 3 ml of 1N NaOH are added. The mixture is stirred at 60° C. for 30 minutes, then acidified with HOAc and diluted with 25 ml of saturated aqueous NaCl solution. The suspension is extracted with EtOAc (5× 10 ml) and concentrated under reduced pressure at 45° C. and chromatographed by preparative TLC using the solvent system $CHCl_3$/MeOH/HOAc (92.5+7.5+0.5). The major band is eluted with MeOH and the solvent evaporated under reduced pressure at 45° C. The product can be analyzed for homogeneity by TLC, and analyzed by IR spectroscopy and amino-detecting reagents as above.

Example 9

To prepare N-[5-(3'-amino-3'-deoxythymid-3-yl)-valeryloxy] -succinimide (AMT-3-V:NOS), a suspension of 200 mg AMT-3-VA (Example 8) and 80 mg NOS in 5 ml THF is chilled on an ice-MeOH bath, followed by addition of 1 ml DCC. The mixture is stirred 90 minutes while the bath temperature is increased from −12° C. to +15° C., then the mixture is stirred at room temperature for two hours. Analytical TLC using the solvent system $CHCl_3$/MeOH/HOAc (95+5+0.5) can be utilized to approximate the conversion to the active ester or byproducts.

Example 10

The synthesis of AMT-3-valeryl:BSA (AMT-3-V:BSA) can be carried out as follows: a solution of 100 mg bovine serum albumin (BSA) in 25 ml deionized water is chilled on an ice bath and approximately 200 μmoles of AMT-3-V:NOS (Example 9) is added. Stirring on the ice bath is continued while maintaining the pH between 8.0 and 8.5 by adding 5% $K_2CO_3$ until stable (about 2 hours). The solution is stirred an additional 30 minutes at room temperature, centrifuged and chromatographed over Sephadex G-25 (2.5×50 cm bed), equilibrated and eluted with PBS (0.01M $NaPO_4$/0.15M NaCl/pH 7.4).

Example 11

One possible synthesis scheme for AMT-3-valeryl: keyhole limpet hemocyanin (AMT 3-V:KLH) is as follows: keyhole limpet hemocyanin (KLH), 130 mg, is allowed to stand overnight in 30 ml deionized water with occasional stirring, then filtered through glass wool. The filtrate which is subsequently chilled on an ice bath and treated with approximately 200 μmoles AMT-3-V:NOS (Example 9). The mixture is stirred on the ice bath while adding 5% $K_2CO_3$ to maintain the pH between 8.0 and 8.5 until stable (about 2 hours). Three ml of 5% $NaHCO_3$ is added and the pH adjusted with 5% $K_2CO_3$ to 8.4. The suspension is incubated for 24 hours at 4° C. then dialyzed overnight versus cold running deionized water.

Example 12

One method for synthesizing 5-[5-(3'-amino-3'-deoxythymid- 3-yl)-valeramido]-fluorescein (AMT-3-V:FAM) involves the addition to a solution of 10 mg AMT-3-VA (Example 8), of 10 mg fluoresceinamine Isomer I (FAM), 1.5 µl concentrated HCl in 2.5 ml acetone, and 50 µmoles DCC, being stirred for 30 minutes at room temperature.

Example 13

To synthesize 5-[5-(3'-amino-3'-deoxythymid- 3-yl)-valeramido]-ethylthiocarbamyl]-fluor escein (AMT-3-V:FTED), a solution of 10 mg FTED in 1 ml DMA is chilled on an ice bath and treated with approximately 14 µmoles of AMT-3-V:NOS (Example 9). The solution is stirred 15 minutes on the ice bath, then three hours at room temperature. The mixture is diluted with 10 ml deionized water and acidified with HCl to precipitate the crude product which is partially purified by preparative TLC using the solvent system $CHCl_3$/MeOH/HOAc (80+20+1).

Example 14

One synthesis scheme for AMT-3-valeryl:RSA (AMT-3-V:RSA) is as follows: a solution of 100 mg rabbit serum albumin (RSA) and 150 mg $NaHCO_3$ in 15 ml deionized water is treated with approximately 35 µmoles AMT-3-V:NOS (Example 9) after chilling on an ice bath. The pH is adjusted to 8.5 with 5% $K_2CO_3$ and the mixture incubated overnight at 4° C. The mixture is filtered through a 1.2 µm membrane and chromatographed over Sephadex G-25 (2.5× 50 cm bed), and eluted with 0.01M $NaPO_4$/0.15M NaCl/pH 7.4/0.1% $NaN_3$.

Example 15

The synthesis of AMT-3-valeryl:horseradish peroxidase (AMT-3-V:HRPO) can be carried out as follows: a solution of 15 mg (40 umoles) of AMT-3-VA (Example 8), 10 mg NOS (87 umoles) and 10 mg DCC (50 umoles) in 200 µl of dry DMA is stirred for two hours at room temperature. Analytical TLC using a solvent system of $CHCl_3$/MeOH/HOAc (95+5+0.5) can be used to monitor the conversion to the active ester. The reaction mixture is added to a solution of 13 mg horseradish peroxidase dissolved in 2 ml of 0.15M borax-HCl, pH 8.5 which has been prechilled on an ice bath. The mixture is stirred 30 minutes on the ice bath, then filtered through a 0.45 µm polytetrafluorethylene (PTFE) membrane to remove dicyclohexylurea. The clear filtrate is chromatographed over a 1×30 cm column of Sephadex G-25, eluted with PBS (0.01M $NaPO_4$/0.15M NaCl/pH 7.4). The protein peak is filtered through a 0.2 µm membrane and the filtrate stored at −20° C. The presence of peroxidase activity can be scored by a qualitative color reaction.

Example 16

To Synthesize 5'-O-dimethylthexylsily-3'-amino-3'-deoxythymidine (AMT-5'-TDS), A suspension of 500 mg AMT and 200 mg of imidazole in 15 ml of DMF is chilled on an ice-bath, followed by addition of 420 µl of dimethylthexylsilyl chloride. The mixture is stirred overnight. Analytical TLC is performed on silica gel-F 250 µm using a solvent system ($CH_2Cl_2$/MeOH ($NH_3$) 95:5) to demonstrate that no AMT remains in the reaction mixture. AMT 5'-TDS is extracted with ethyl acetate (3×30 ml), washed ($H_2O$, 20 ml), dried ($Na_2SO_4$) and concentrated invacuo to give 750 mg of a white crystalline solid of AMT-5'-TDS.

Example 17

To synthesize 5'-O-dimethylthexylsilyl-5-hydroxymethyl-AMT derivitive (AMT-5'-TDS-5-HM), a mixture of 700 mg AMT-5'-TDS and 440 mg N-bromosuccinimide in dry carbon tetrachloride (20 ml) is heated under reflux in an $N_2$ atmosphere for 1 h and simultaneously is exposed to light (provided by a 150-W flood lamp). The mixture is filtered and the filtrate is concentrated in vacuo to give a crude α-bromide, which is dissolved in THF (15 ml). A solution of $NaHCO_3$ (200 mg) in $H_2O$ (5 ml) is added and the mixture is stirred overnight at room temperature and then extracted with chloroform (3×15 ml). The combined organic extracts are washed ($H_2O$, 25 ml), dried ($Na_2SO_4$), and concentrated in vacuo. The residue is chromatographed on a silica gel column ($CH_2H_2$/MeOH 90:10) to give 420 mg of AMT-5'-TDS-5-HM.

Example 18

To synthesize 5'-O-thexyldimethylsilyl-5-carboxyl-AMT derivitive (AMT-5'-TDS-5-CA), Jones reagent (1 ml) is added drop-wise to a stirred solution of 400 mg AMT 5'-TDS-5-HM in acetone (20 ml) at 10°–15° C. Stirring is continued for 2 h at ambient temperature. The reaction slurry is cooled to 10° C. and treated with iso-propanol (10 ml). The reaction is then filtered through celite. The filtrate is concentrated to give a solid residue. The IR spectrum demonstrate an absorption band at 1700 $cm^{-1}$ characteristic of β-unsaturated carboxyl group.

Example 19

To synthesize 5-carboxyl-AMT derivative (AMT-5-CA), to a solution of 350 mg AMT 5'-TDS-5-CA in 20 ml THF, is added 1 ml of 1M tetrabutylammonium fluoride in THF. The reaction is stirred for 1 h and then neutralized with 1N HCl. The mixture reaction is evaporated and the residue is chromatographed on a silica gel column ($CH_2H_2$/MeOH ($NH_3$) 90:10) to give 170 mg of AMT 5-CA.

Example 20

To synthesize 5-N-carboxyl-succinimide AMT derivative (AMT-5-C:NOS) a suspension of 150 mg of AMT 5-CA and 70 mg N-hydroxysuccinimide (NOS) in 5 ml tetrahydrofuran is chilled on an ice-MeOH bath, followed by addition of 0.8 ml 1,3-dicyclohexylcarbodiimide (DCC, 1M in THF). The mixture is stirred at room temperature for 3 hours. Analytical TLC on silica gel-F 250 µm using the solvent system ($CHCl_3$/MeOH ($NH_3$) 90:10) shows approximately 80% to the active ester with no byproducts.

In addition to the examples above demonstrating the activation of the 5-methyl group as a methoxy derivative, other processes for activating this position for derivatization will be apparent to the skilled Artisan. For example, activation as a methylhalogen would be suitable for derivatization. 5-carboxypropionyl AMT derivatives can be obtain by reacting 5-bromomethyl AMT derivative with diethylmalonate, followed by hydrolysis of the diester, and heat decarboxylaton.

Example 21

To conjugated AMT-5-carboxyl to BSA (AMT-5-C:BSA) a solution of 80 mg bovine serum albumin (BSA) in 20 ml dionized water is chilled on an ice bath and approximately 150 µmoles of AZT-3-C:NOS are added. Stirring on the ice bath is continued while maintaining the pH between 8.0 and 8.5 by adding 5% $K_2CO_3$ until stable (about 2 hours).

Stirring an additional 45 minutes at room temperature gives a slightly turbid solution which is clarified by centrifugation and chromatographed over Sephadex G-25 (2.5×50 cm bed), equilibrated and eluted with PBS (0.01M NaPO4/0.15M NaCl/pH 7.4). The protein peak is diluted with PBS to a biuret value of 1 mg/ml stored at −20° C. in 2 ml aliquots. An aliquot of the above, rechromatographed over G-25 has a similar incorporation of 5 to 15 mols, hapten/66,000 g protein, which did not change after a third passage through G-25.

Other methods for derivatizing and conjugating AMT to carriers and labels will be apparent to those skilled in the art. For instance, Erlanger et al. (1973) Pharmacological Reviews 25:271, incorporated by reference herein, teaches the general methodology of preparing drug:protein conjugates for immunological studies.

Polyclonal Antibodies to AMT

To prepare polyclonal rabbit antibodies to AMT, the immunogen (1 mg in 1 ml) is emulsified with an equal volume of Freund's Complete Adjuvant and injected intradermally into each rabbit. The process is repeated after two weeks. Two weeks later, monthly subcutaneous booster injections are begun with 0.5 mg in 0.5 ml of the immunogen and 0.5 ml of Freund's Incomplete Adjuvant per animal. The rabbits are bled biweekly by a marginal ear vein technique beginning six weeks after the primary immunization. The blood collected is refrigerated, allowing clots to form, and the supernatant (antiserum) retained. The antiserum from each rabbit is collected and stored, either at −20° C. without preservative, or at 4° C. after addition of sodium azide to a final concentration of 0.1%. The same schedule is followed for each immunogen. Rabbits immunized produced antibodies to AMT.

Monoclonal antibodies to AMT

Monoclonal antibodies to AMT or active fragments of such antibodies can be generated by applying generally known fusion cell techniques (cf. G. Kohler, C. Milstein, Vol 6, *Eur J Immunol*, pp 511–519 (1976) and M. Shulmen et al., vol 276, *Nature* pp 269–270 (1978) herein incorporated by reference) to obtain a hybridoma producing the antibody, by deriving a monoclonal antibody from the hybridoma, and (optionally) by subjecting the monoclonal antibody to proteolysis to obtain the active Fab fragment.

Monoclonal antibodies are prepared by obtaining mammalian lymphocytes (preferably spleen cells), committing the lymphocytes to produce antibodies (e.g., by immunizing the mammal with the particular antigenic determinant of interest beforehand), fusing the lymphocytes with myeloma (or other immortal) cells to form hybrid cells, and then culturing a selected hybrid cell colony in vivo or in vitro to yield antibodies which are identical in structure and specificity.

In particular, monoclonal antibodies to AMT can be raised by employing AMT or an analog as an antigen. Mice or other animals can be challenged by injection with a solution of AMT-immunogen in complete Freund's adjuvant at weekly intervals. After the initial injection, the booster injections can be administered without adjuvant or emulsified in incomplete Freund's adjuvant.

Serum samples from the immunized animal can be taken and analyzed by an immunoassay like those described herein to detect the presence of antibodies cross-reactive with AMT. Animals that exhibit antibody titers are sacrificed and their spleens homogenized. Alternatively, the spleen cells can be extracted and the antibody-secreting cells expanded in vitro by culturing with a nutrient medium. The spleen cells are then fused with myeloma (or other immortal) cells by the above-referenced procedure of Kohler and Milstein. The hybridomas so produced are screened (i.e., cloned by the limiting dilution procedure of the above-referenced Baker et al. article) to select a cell producing antibodies which react specifically with AMT and not with AZT. Large scale antibody production can be obtained from such cell lines by various techniques, including the induction of ascites tumors (e.g., after priming with pristane) and the purification of such antibodies from the ascites fluid by Protein A-Sepharose affinity chromatography.

For a further description of general hybridoma production methods, see Oi and Herzenberg, "Immunoglobulin-Producing Hybrid Cell Lines" in *Selected Methods in Cellular Immunology* (Mishell and Shiigi, Ed., W. H. Freeman & Co., 1980) and Scearce and Eisenbarth, "Production of Monoclonal Antibodies . . ." in vol 103 *Methods in Enzymology,* pp 459–469 (1983), and U.S. Pat. No. 4,411,933 issued to Gillis on Oct. 25, 1986, herein incorporated by reference. Human antibodies (i.e., those obtained from human-human or human-animal hybridoma) can be used as well as animal antibodies. For descriptions of human hybridoma production techniques, see U.S. Pat. No. 4,451,570 issued to Royston et al. on May 29, 1984; U.S. Pat. No. 4,529,694 issued to Lazarus et al. on Jul. 16, 1985 and Zurawski et al., "Continuously Proliferating Human Cell Lines Synthesizing Antibody of Predetermined Specificity" in *Monoclonal Antibodies* (Plenum Press, New York 1980), also incorporated by reference.

Active fragments can be derived from the monoclonal antibodies disclosed herein by a number of techniques. For example, purified monoclonal antibodies can be cleaved with an enzyme, such as pepsin and subjected to HPLC gel filtration. The appropriate fraction containing Fab can then be collected and concentrated by membrane filtration or the like. For further description of general techniques for the isolation of active fragments, see for example, Khaw, BA et al., Vol 23 *J Nucl Med.*, pp. 1011–1019 (1982), incorporated by reference.

Radioimmunoassay for AMT

A preferred immunoassay is a radioimmunoassay (RIA), wherein the AMT analog tracer is labeled with a radioactive isotope to facilitate detection. The following procedure illustrates the use of an RIA for determining the concentration of AMT in a sample.

(1) 100 µl of AMT sample (standard or unknown) is added to a 12×75 mm polypropylene tube. 200 µl of buffer (50 mM $KH_2PO_4$, 0.9% NaCL, 10 mM $Na_2$ EDTA, and 0.01% ethylmercurothiosalicyclic acid, pH 7.5), 100 µl of radioactive antigen ($^3$H-AMT), and 100 ml of anti-AMT antibody solution is added to the tube, votexed, and incubated overnight at 4° C.

(2) After incubation, 50 µl of cold labile enzyme-free bovine gamma globulin (LEF-BGG) (10 mg/ml) is added as the carrier protein, followed by 550 µl of cold saturated ammonium sulphate in water (pH 7.5 at 4° C.). The tubes are mixed and held at 4° C. for about 1 hour.

(3) The tubes are centrifuged at 4° C. to collect the precipitate, the supernatant being discarded. The precipitate is washed with cold, half-saturated ammonium sulphate.

(4) The precipitate is dissolved in 0.1 ml of deionized water, 0.1 ml of 4N HCl is then added followed by 2.5 ml of a suitable scintilation containing fluid, vortexed and counted in the appropriate acintillation counter.

To obtain a standard curve, known amounts of cold AMT in buffer are assayed as part of this competitive binding assay with the radiolabeled AMT. The amount of AMT present in the unknown sample can then be interpolated from the standard curve.

Variations of this technique are known to the skilled artisan and include the use of a secondary antibody directed to the constant region of the anti-AMT antibody as a means of precipitating the anti-AMT antibody:AMT complex instead of ammonium sulphate. Alternatively, the anti-AMT antibody can be immobilized on an insoluble carrier such as the well of a microtiter plate or on the surface of a polystyrene bead.

Fluorescence Polarization Immunoassay for AMT

The following procedure illustrates the use of various materials of the invention in a preferred FPIA method.

(1) 50–250 ul AMT sample (standard or unknown) is added per microcentrifuge tube. An equal volume of precipitation reagent is added per microcentrifuge tube. The tubes are centrifuged at greater than 9,000×g for 1 minute.

(2) A 17.5 ul sample of each serum extract is brought to approximately pH 7–8 by the addition of buffer.

(3) 25 ul each of AMT antibodies and AMT tracer are added per tube and the volume per tube brought to approximately 2 ml with buffer.

(4) After an appropriate incubation time, the polarization of each reaction mixture is determined using a polarization spectrofluorimeter.

A plot of polarization versus AMT concentration for a set of AMT standards can be used to determine the concentration of AMT in unknowns by interpolation.

AMT Microtiter Plate Enzyme Immunoassay

To each well of a 96 well microtiter plate is added 100 ul of diluted anti-AMT antibodies. After incubation overnight, the plate is washed, and 300 ul of diluted normal rabbit serum is added to each well to block any unbound sites on the plastic surface of the microtiter plate. The plate is again washed and the excess moisture removed. Next, 50 ul of AMT sample is added to the appropriate well followed by the addition of 50 ul of AMT-3-V:HRPO (Example 17) to all wells. The plate is incubated for 60 minutes at room temperature. The plate is then washed and 300 ul of diluted o-phenylenediaminehydrogen peroxide substrate solution is added to each well. The color is allowed to develop for 90 minutes at room temperature in the dark. Absorbances are then measured spectrophotometrically for each well. A plot of absorbance versus AMT concentration for a set of AMT standards can be used to determine the concentration of AMT in unknown samples by interpolation.

Although this invention has been described in some detail and by way of various specific examples in order to illustrate the invention, it will be apparent that various equivalents, changes and modifications may be made without departing from the spirit and scope thereof.

What is claimed is:

1. A method for analyzing a sample of human plasma to determine the presence of 3'-amino-3'-deoxythymidine (AMT), comprising the steps of providing a sample of human plasma suspected of containing AMT;

mixing with the sample (i) a tracer compound comprising an analog of AMT having attached thereto a label group able to be detected, and (ii) an antibody having a high degree of specificity to AMT and no cross-reactivity with 3'-azido-3'-deoxythymidine (AZT);

determining the amount of tracer compound bound to the antibody; and calculating the amount of AMT present in the sample based on the amount of tracer compound bound to the antibody.

2. The method of claim 1 wherein the label group is selected from the group consisting of radioisotopes, fluorescent compounds, enzymes, and enzyme co-factors.

3. The method of claim 1 wherein the analog of AMT is represented by the general formula

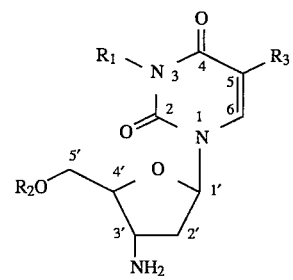

where $R_3$ is methyl or hydrogen and one of $R_1$ and $R_2$ is hydrogen and the other is R-X, or where $R_1$ and $R_2$ are hydrogen and $R_3$ is R-X, where R is a linking group and X is a label group.

4. The method of claim 3 wherein R is selected from the group consisting of alkyl, carboxyl, carbonyl, monoxocarbonyl, hydroxy, alkoxy, amido, halo, thiocarbonyl, cyano, nitrilo, thio, imino, amino, carbalkoxy, mercuri, phthalimido, formyl, Keto, succinimidoxy, succinyl, thiocarbamyl, azo, hydroxyphenyl, and imidazolyl.

5. The method of claim 3 wherein X is selected from the group consisting of horseradish peroxidase, alkaline phosphatase, β-galactosidase, luciferase, urease, fluorescein and analogs thereof, rhodamine and analogs thereof, allophycocyanin, R-phycoerythrin, erythrosin, europium, luminol, luciferin, coumarin analogs, $^{125}I$, $^{131}I$, $^{3}H$, $^{35}S$, $^{14}C$ and $^{32}P$.

6. The method of claim 1 wherein the analog of AMT is tritiated AMT, with tritium serving as the label group.

7. The method of claim 1 wherein the analog of AMT comprises an AMT molecule having $^{14}C$ incorporated therein and serving as the label group.

8. The method of claim 1 wherein the assay is of sufficient sensitivity to detect AMT within the sample at concentrations as low as 0.1 to 1.0 ng/ml.

9. The method of claim 1 wherein the method further comprises measuring the level of the 5'-O-glucuronide of AMT (GMAT) in the sample, following the measurement of measuring AMT levels, comprising the steps of treating the sample with β-glucuronidase to remove the 5'-O-glucuronide moiety;

measuring the level of AMT following the removal of the 5'-O-glucuronide moiety; and calculating the difference of the amount of AMT present in the sample as first measured and the amount of AMT present in the sample as measured after the removal of the 5'-O-glucuronide moiety, the difference representing the quantity of GAMT present in the sample.

10. A method for analyzing a sample of human plasma to determine the presence of 3'-amino-3'-deoxythymidine (AMT), comprising the steps of providing a sample of human plasma suspected of containing AMT;

mixing with the sample (i) a competitor compound comprising AMT or an analog thereof, and (ii) an AMT-specific antibody having a high degree of specificity for AMT and no cross-reactivity with 3'-azido-3'-deoxythymidine (AZT);

determining the amount of competitor compound bound to the AMT-specific antibody; and calculating the amount of AMT present in the sample based on the amount of competitor compound bound to the AMT-specific antibody.

11. The method of claim 10, wherein the competitor compound comprises an analog of AMT having attached thereto a label group able to be detected, and the amount of competitor compound bound to the AMT-specific antibody is determined by detecting the label group.

12. The method of claim 10, wherein the AMT-specific antibody further comprises a label group attached thereto and able to be detected, and the amount of competitor compound bound to the AMT-specific antibody is determined by detecting the label group.

13. The method of claim 10, further comprising a labeled secondary antibody directed against the AMT-specific antibody, wherein the secondary antibody includes a label group attached thereto and able to be detected, and the amount of competitor compound bound to the AMT-specific antibody is determined by detecting the labeled secondary antibody.

* * * * *